US006653457B1

(12) United States Patent
Larm et al.

(10) Patent No.: US 6,653,457 B1
(45) Date of Patent: Nov. 25, 2003

(54) METHOD OF COVALENT COUPLING

(75) Inventors: Olle Larm, Bromma (SE); Ibrahim Gouda, Sollentuna (SE)

(73) Assignee: Medicarb AB, Bromma (SE)

( * ) Notice: Subject to any disclaimer, the term of this patent is extended or adjusted under 35 U.S.C. 154(b) by 0 days.

(21) Appl. No.: 10/130,312

(22) PCT Filed: Nov. 9, 2000

(86) PCT No.: PCT/SE00/02198

§ 371 (c)(1),
(2), (4) Date: Jun. 27, 2002

(87) PCT Pub. No.: WO01/37893

PCT Pub. Date: May 31, 2001

(30) Foreign Application Priority Data

Nov. 23, 1999 (SE) ................................. 9904241

(51) Int. Cl.$^7$ ........................... C08B 37/10; C08B 37/00
(52) U.S. Cl. ....................... 536/20; 536/123.1; 536/124; 536/55.1; 536/55.3; 525/54.2
(58) Field of Search .................. 536/21, 124, 55.1, 536/55.3, 123.1; 525/54.2

(56) References Cited

U.S. PATENT DOCUMENTS

| 4,613,665 A | * | 9/1986 | Larm |
| 5,529,986 A | | 6/1996 | Larsson et al. |
| 5,679,659 A | | 10/1997 | Verhoeven et al. |
| 5,728,420 A | | 3/1998 | Keogh |

FOREIGN PATENT DOCUMENTS

| WO | 88/00211 | 1/1988 |
| WO | 93/24503 | 12/1993 |
| WO | 99/33499 | 7/1999 |
| WO | 00/13718 | 3/2000 |

OTHER PUBLICATIONS

Derwent's abstract, Accession No. 1988–342368, week 8838, Abstract of JP, 63255299. (Snow Brand Milk Prod. Co. Ltd., Oct. 21, 1988.

* cited by examiner

Primary Examiner—Samuel Barts
Assistant Examiner—Michael C. Henry
(74) Attorney, Agent, or Firm—Burns, Doane, Swecker & Mathis, L.L.P.

(57) ABSTRACT

A method of preparing conjugates by means of covalent coupling of a polysaccharide selected from heparin, heparin derivatives, at least partially deacerylated dermatan sulphate and dextran sulphate and a solid substance containing primary amino groups, said method comprising the following steps: a) reduction of the saccharide so that its terminal monosaccharide unit is converted to an alditol; b) periodate oxidation of the alditol formed in step a) to the formation of a terminal aldehyde group under cleavage of the monosaccharide unit between two vicinal groups selected from hydroxyl and amino groups; and c) reductive coupling of the alditol via the aldehyde group to the amino group of the solid substrate.

21 Claims, No Drawings

METHOD OF COVALENT COUPLING

This is the National Phase Application of PCT/SE00/02198 filed Nov. 9, 2000.

TECHNICAL AREA

The present invention relates to the manufacture of conjugates between oligo- or polysaccharides and aminated substrates. The invention also covers the products hereby obtained.

BACKGROUND OF THE INVENTION

Covalent coupling of saccharides to substrates can be made mainly in two different ways, on the one hand through so-called "end-point attachment" (EPA), on the other hand by so-called "multipoint attachment" (MPA). In the first case the saccharide is coupled via its terminal reducing monosaccharide unit. In the second case, which is relevant with polysaccharides, it is coupled via several monosaccharide units inside the polysaccharide. Most of the high molecular carbohydrates present in nature, which are coupled to some other high molecular compound, are immobilized via their reducing monosaccharide unit, and such natural conjugates are for example glycoproteins, glycolipides, proteoglycines and lipopolysaccharides.

Coupling via "end-point attachment" means contrary to "multipoint attachment" that the molecule in an immobilized state to a high degree maintains its natural conformation and thereby maintains its capacity to specifically interact with other molecules, such as plasma proteins, growth factors, antibodies, lectins and enzymes.

For reductive coupling to aminated substrates of polysaccharides one has tried to make use of the aldehyde functions in terminal reducing monosaccharide units. However, these aldehyde functions are present as hemi-acetals, which means that the aldehyde function has extremely low reactivity resulting in unacceptably low coupling yields in most cases.

A useful method for "end-point attachment" of polysaccharides to aminated surfaces is described in U.S. Pat. No. 4,613,665.

This known method is briefly constituted by partial degradation of a polysaccharide-containing D-glucosamine or D-galactosamine units, for example heparin, with sodium nitrite in an acid environment. This results in the formation of 2,5-anhydro-D-mannose units as reducing terminal units. This reducing terminal unit carries a reactive aldehyde function, which is not engaged in any hemi-acetal formation and, accordingly the aldehyde group can in high yield by reductive amination be coupled to substrates containing primary amino groups.

This known method is associated with certain drawbacks, among which the following can be mentioned.

The method requires that the polysaccharide contains D-glucosamine or D-galactosamine units with non-derivatizing and thereby primary amino groups capable of diazotization.

In the activation the molecule is degraded which for certain applications results in lost or substantially reduced biological activity.

The method also means that only half of the molecules formed in the degradation obtain a reducing end capable of coupling.

SUMMARY OF THE INVENTION

The present invention has for a main object to provide a new method whereby the disadvantages of the prior art are eliminated or at least essentially reduced.

Yet another object of the invention is to provide a method in which the substance subject to coupling to an aminated substrate will not be degraded or damaged in connection to the coupling procedure, whereby the properties of the substance are maintained substantially unchanged after the coupling to the substrate has taken place.

Yet another object of the invention is to provide a method where all molecules are made subject to coupling, whereby the yield in the coupling reaction is substantially improved compared to the prior art.

A further object of the invention is to provide a process which involves "end-point" coupling to aminated substrates.

For these and other objects which will be clear from the following disclosure there is provided through the present invention a method of preparing conjugates by means of covalent coupling of a polysaccharide selected from heparin, heparin derivatives, at least partially deacetylated dermatan sulphate and dextran sulphate and a solid substance containing primary amino groups. Accordingly, the method according to the invention is a method of heterogeneous character characterized by the following steps:

a) reduction of the saccharide so that its terminal monosaccharide unit is converted to an alditol;

b) periodate oxidation of the alditol formed in step a) to the formation of a terminal aldehyde group under cleavage of the monosaccharide unit between two vicinal groups selected from hydroxyl and amino groups; and c) reductive coupling of said alditol via the aldehyde group to the amino group of the solid substrate.

The reduction in step a) above is suitably carried out with the reducing agent selected from borohydrides, catalytic reducing agents and Raney nickel. It is particularly preferred to carry out the reduction in step a) with a borohydride, especially sodium borohydride or potassium borohydride.

With regard to the oxidation in step b) above it is suitably carried out with periodic acid or a sodium or potassium salt thereof.

The reductive coupling in step c) above is suitably carried out with a cyanoborohydride, for example sodium cyanoborohydride or potassium cyanoborohydride.

A preferred embodiment of the method according to the invention thus means that the reduction in step a) is carried out with sodium borohydride, the oxidation in step b) is carried out with sodium periodate and the reductive coupling in step c) is carried out with sodium cyanoborohydride.

The method according to the present invention is particularly suited to be used in connection with polysaccharides possessing biological activity. Thus, the polysaccharide may be selected from heparin, heparin derivatives, at least partially deacetylated dermatan sulphate and dextran sulphate. Particularly preferred polysaccharides are heparin and heparan sulphate.

With regard to the character of the substrate there may be mentioned as examples of substrates aminated plastic objects, for example having surface coatings of polyethylenimine or chitosan. Preferred surface coating is chitosan which in its capacity as a deacetylated chitin contains primary amino groups suited for the coupling techniques involved in the present invention.

The invention also includes conjugates made by the method defined above.

The reactions involved in the method according to the present invention will now be further elucidated for a better understanding of the reaction mechanisms.

The periodate oxidation in step b) above involves the formation of a cyclic ester which is then cleaved and inter alia results in two aldehyde functions according to formula I below.

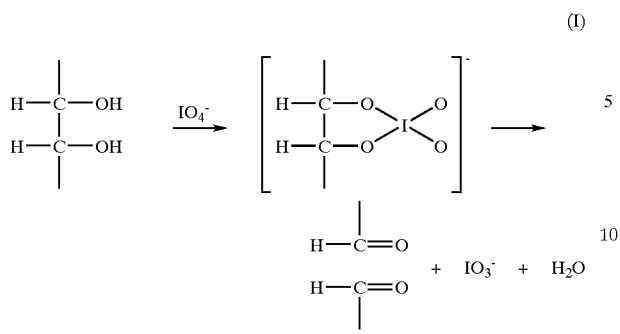

(I)

Cleavage of vicinal dioles by periodate oxidation is previously known but as far as is known it has not previously been applied to saccharide immobilization in accordance with the present invention. In the reaction steric factors have a decisive influence on the rate by which different vicinal dioles are cleaved by periodate.

Thus, vicinal OH-groups in furanosides and pyranosides which have cis-orientation are more rapidly cleaved than such having trans-orientation. Certain trans-dioles in rigid systems are even resistant to periodate oxidation. Acyclic dioles are generally oxidized more rapidly than cyclic compounds, and such of threo-configuration are more rapidly oxidized than such with erythro-configuration.

The invention will even if it is not restricted hereto be exemplified in the following with reference to heparin. Formula II below describes a representative part of the interior of the heparin molecule. The left D-glucosamine unit wherein R is acetyl, cannot be oxidized with periodate. Of the other units only the glucuronacid unit is capable of oxidation but contains, however, dioles oriented trans-di-equatorially and difficult to oxidate.

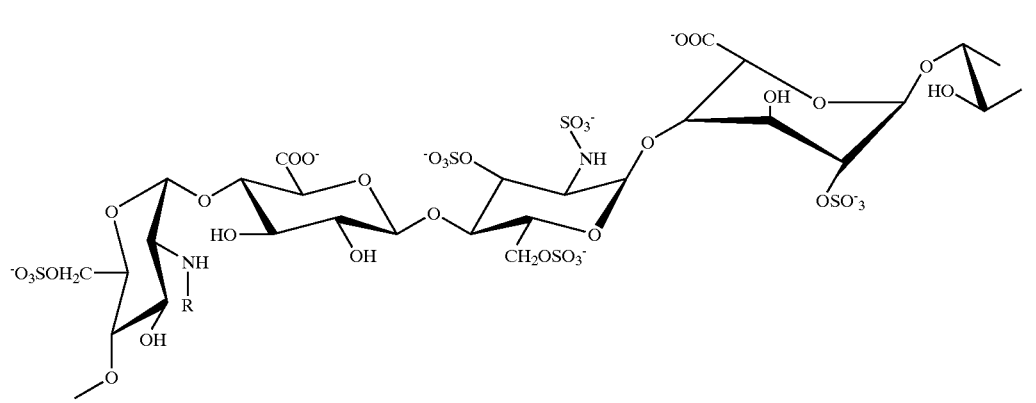

(II)

The major part of the molecules in native heparin having a molecular weight of between about 7000 and about 25000 contains terminally the following sequence:

- - - 4) -α-D-GlcpNR- (1 - - - 4) -β-D-GlcA,
    wherein R is acetyl or —$SO_3H$.

The terminal group can be reduced to the alditol of formula III below, the pH value suitably being maintained so high as not to lactonize the acid. By cautious periodate oxidation the threo-glycol grouping is preferably oxidized and a compound of formula IV containing a terminal aldehyde group will be obtained.

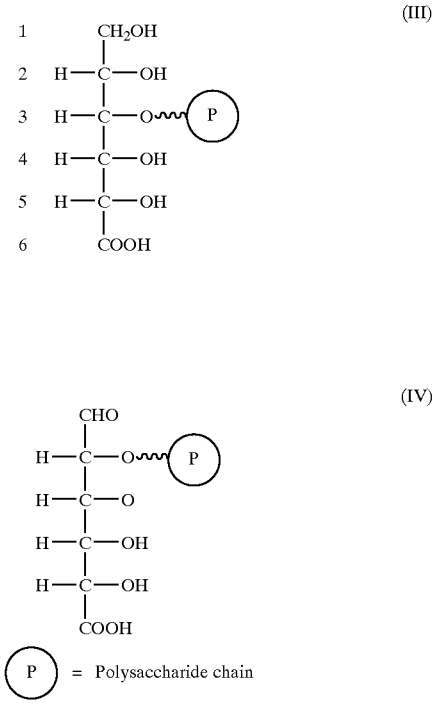

(III)

(IV)

$\left(P\right)$ = Polysaccharide chain

The reaction can possibly proceed further to the formation of an aldehyde function of C-atom 5.

The relevant polysaccharides are then coupled to a solid substrate containing primary amino groups by reductive amination in accordance with formula V below.

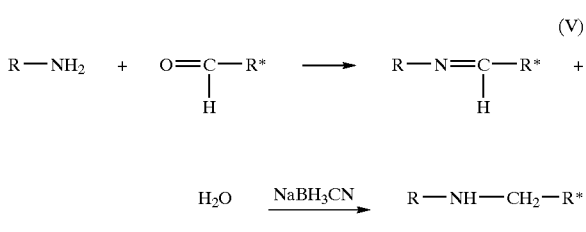

(V)

In an analogous manner for example chitosan can be immobilized by "end-point" -coupling according to formula VI below.

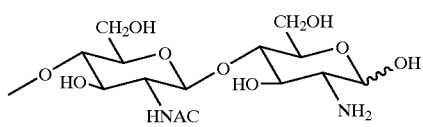

Here vicinally oriented amino and hydroxyl groups are oxidized by periodate according to formula VII below.

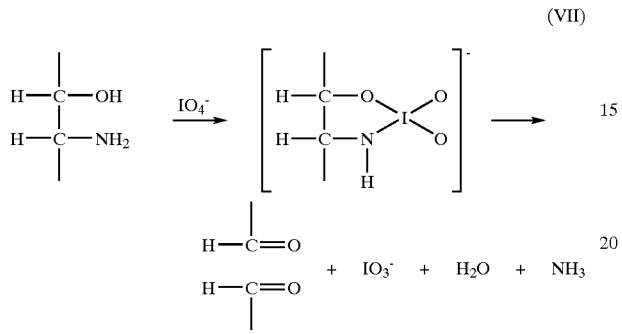

The reactions involved in the present invention are by formulae shown on the appended scheme. P within a ring designates the polymer or the polysaccharide, whereas only the structure of the terminal unit has been illustrated. COOH in 6-position refers to polysaccharides having a terminal glucuronic acid unit, whereas $CH_2OH$ in 6-position relates to polysaccharides having glucosamine units in terminal position.

The coupling techniques according to the present invention constitute an essential contribution to the possibility of immobilizing polysaccharides to aminated solid substrates while maintaining the original properties of the saccharide, for example biologic activity.

The invention will in the following be illustrated further by non-limiting examples, wherein parts and percentages relate to weight if not otherwise stated.

EXAMPLE 1

Reductive-oxidative Activation of Native Heparin

Sodium borohydride (225 mg) is dissolved in distilled water (150 mL). The sodium salt of native heparin (Pig mucosa, Kabi Vitrum, 3 g) is added, and the reaction mixture is allowed to stand under stirring for 18 hours. After dialysis against 10 L distilled water for 18 hours the reduced heparin is freeze-dried and the yield is 2,9 g.

The reduced heparin (2,9 g) is dissolved in 250 mL imidazole buffer, 40 mM, pH 6,5. Sodium periodate (640 mg) is also dissolved in 250 mL imidazole buffer 40 mM, pH 6,5. The two solutions are mixed and are allowed to stand in a flask enclosed in foil at 0° C. on ice under stirring for 5 minutes. Then 1 mL glycerol is added for the purpose of destroying the excess periodate, and the solution is allowed to stand under stirring for 1 hour. The reaction mixture is then dialysed against 10 L distilled water for 18 hours and the heparin is finally freeze-dried. The yield of activated heparin (RO-heparin) is 2,4 g.

EXAMPLE 2

Decomposition of Heparin With Nitrous Acid

Heparin (Pig mucosa, Kabi Vitrum) is dissolved in water (300 ML). The solution is cooled to and maintained 25 at 0° C. in ice-water. Then first sodium nitrate ($NaNO_2$, 10 mg) and then acetic acid (2 mL) are added to the solution under stirring. The reaction mixture is maintained at 0° C. for 2 hours, dialysed and freeze-dried. The yield of degraded heparin is 0,7 g.

EXAMPLE 3

Periodate Oxidation of Native Heparin

In a typical example, where 10% of the monosaccharide units in heparin are to be oxidized, native heparin (Pig mucosa, Kabi Vitrum, 5 g) is dissolved in water (100 mL) and sodium periodate (0,5 g) is added. The solution is kept in the dark at room temperature for 24 hours. The reaction mixture is dialysed against distilled water and freeze-dried to the formation of 4,2 g heparin derivative containing dialdehyd-functions.

EXAMPLE 4

Amination of a Polyethylene Surface With Polyethylenimine (PEI)

A polyethylene surface (polyethylene film) is treated for 2 minutes at room temperature with 2% (w/v) solution of sodium permanganate in concentrated sulphuric acid and is then carefully rinsed with distilled water. The polymer surface is treated at room temperature with polyethylenimine SN (PEI, 0,05% in borate buffer, pH 9,0) together with crotonaldehyde (0,034% in borate buffer, pH 9,0).

The polymer surface is carefully rinsed with large volumes of distilled water and treated with the solution of dextran sulphate (Pharmacia) 0,1 g/L in 0,15 M NaCl, pH 3,0, for 10 minutes at 55° C. The polymer surface is again carefully rinsed with large volumes of distilled water and treated once again at room temperature with polyethylenimine SN (PEI, 0,05% in borate buffer, pH 9,0) together with crotonaldehyde (0,034% in borate buffer, pH 9,0). The treatment with dextran sulphate according to the above is then repeated and the surface is carefully rinsed with distilled water and treated with a solution of 0,05% PEI at pH 9,0 (adjusted with 1 M NaOH) for 10 minutes at room temperature and then again washed. The presence of amino groups is verified with an indicator (poinceau S, Sigma).

EXAMPLE 5

Amination of Polyethylene Surface With Chitosan

A polyethylene surface is treated in the same manner as in Example 4 with the difference that a solution of chitosan having a degree of N-acetylation of 15% (0,25 w/v) in water is used instead of PEI and that the surface after treatment with this solution is rinsed with ethanol (80% v/v) instead of water. The presence of amino groups is verified in the same manner as in Example 4.

EXAMPLE 6

Coupling of RO-heparin to Flexible Polyethylene Tubings

Polyethylene tubings (1 m, 1,8 mm inner diameter) are aminated in the manner described in Example 4. The tubings are then treated for 2 hours at 50° C. with RO-heparin prepared in accordance with Example 1 (500 mL, 0,025% w/v) and sodium cyanoborohydride (0,003% w/v in 0,15 M NaCl, pH 3,9) and are washed with distilled water and finally with borate buffer, pH 9,0. The presence of heparin on the polyethylene tubings is visualized using an indicator, Toluidine blue, giving a lilac colour in the presence of sulphated polysaccharides.

EXAMPLE 7

Coupling of Nitrite-degraded Heparin to Flexible Polyethylene Tubings

This coupling is carried out in accordance with Example 6 above with the modification that nitrite-degraded heparin prepared in accordance with Example 2 is used in the coupling. With regards to details concerning this coupling technique reference is made to U.S. Pat. No. 4,613,665.

EXAMPLE 8

Coupling of Periodate Oxidized Heparin to Flexible Polyethylene Tubings

This coupling is carried out in accordance with Example 6 above but with the modification that periodate-oxidized heparin prepared in accordance with Example 3 is used in the coupling procedure.

EXAMPLE 9

Comparing Studies of AT-uptake

The ability of the heparin surface to bind antithrombin (AT) reflects the density of heparin molecules having unaffected AT-binding sequences and constitutes a measure of the non-thrombogenic character of the surface. The larger the ability to bind antithrombin the better the surface is with regard to the biological activity of the heparin.

TABLE

|  | Control* | Ex 6 | Ex 7 | Ex 8 |
| --- | --- | --- | --- | --- |
| AT pmol/cm$^2$ | 0, 02 | 2, 8 | 2, 6 | 0, 9 |

*control using untreated tubing

EXAMPLE 10

Coupling of Reductively-oxidatively Activated Dextran Sulphate to Polyethylene Film Sodium borohydride (225 mg) is dissolved in distilled water (150 mL). The sodium salt of dextran sulphate (4 g, Pharmacia) is added and the reaction mixture is allowed to stand under stirring for 18 hours. After dialysis against 10 L distilled water for 18 hours the reduced dextran sulphate (heparinoide) is freeze-dried and the yield is 3,5 g. The reduced dextran sulphate (3,0 g) is dissolved in 250 mL imidazole buffer, 40 mM, pH 6,5. Sodium periodate (640 mg) is also dissolved in 250 mL imidazole buffer, 40 mM, pH 6,5. The two solutions are mixed and allowed to stand in a flask wrapped in foil at 0° C. on ice under stirring for 5 minutes. Then 1 mL glycerol is added for the purpose of destroying the excess periodate, and the solution is allowed to stand under stirring for 1 hour The reaction mixture is dialysed against 10 L distilled water for 18 hours, and the product is finally freeze-dried. The yield of RO-heparinoide is 2,5 g.

The RO-heparinoide is coupled to an aminated polyethylene film prepared in accordance with Example 4, the coupling is carried out in the same manner as described in Example 6. The presence of dextran sulphate on the polyethylene film is visualized using an indicator, Toluidine blue, giving a lilac colour in the presence of sulphated polysaccharide. The coupling yield is about 5 mg/cm$^2$ (determined using FTIR).

The invention is not restricted to the above embodiments and examples since the method is applicable to covalent coupling of all types of oligo- and polysaccharides having a terminal reducing monosaccharide unit to all forms of substrates containing primary amino groups.

What is claimed is:

1. A method of preparing conjugates by means of covalent coupling of a polysaccharide selected from heparin, heparin derivatives, at least partially deacetylated dermatan sulphate and dextran sulphate and a solid substance containing primary amino groups, comprising the steps:

a) reduction of the saccharide so that its terminal monosaccharide unit is converted to an alditol;

b) periodate oxidation of the alditol formed in step a) to the formation of a terminal aldehyde group under cleavage of the monosaccharide unit between two vicinal groups selected from hydroxyl and amino groups; and c) reductive coupling of said alditol via the aldehyde group to the amino group of the solid substrate.

2. A method according to claim 1, characterized in that the reduction in step a) is carried out with a reducing agent selected from borohydrides, catalytic reducing agents, and Raney nickel.

3. A method according to claim 2, wherein the reduction in step 2) is carried out with a borohydride.

4. A method according to claim 1, wherein the oxidation in step b) is carried out with periodic acid or a sodium or potassium salt thereof.

5. A process according to claim 1, wherein the reductive coupling in step c) is carried out with a cyanoborohydride.

6. A method according to claim 1, wherein the reduction in step a) is carried out with sodium borohydride; the oxidation in step b) is carried out with sodium periodate; and the reductive coupling in step c) is carried out with sodium cyanoborohydride.

7. A method according to claim 1, wherein the saccharide is a polysaccharide which is biologically active.

8. A method according to claim 7, wherein the polysaccharide is heparin or heparan sulphate.

9. A method according to claim 1, wherein the substrate is selected from polymeric objects aminated on the surface thereof.

10. A method according to claim 1, wherein the substrate is provided with a coating of polyethylenimine or chitosan.

11. Conjugate made by the method according to claim 1.

12. A method according to claim 2, wherein the oxidation in step b) is carried out with periodic acid or a sodium or potassium salt thereof.

13. A method according to claim 3, wherein the oxidation in step b) is carried out with periodic acid or a sodium or potassium salt thereof.

14. A process according to claim 2, wherein the reductive coupling in step c) is carried out with a cyanoborohydride.

15. A process according to claim 3, wherein the reductive coupling in step c) is carried out with a cyanoborohydride.

16. A process according to claim 4, wherein the reductive coupling in step c) is carried out with a cyanoborohydride.

17. A method according to claim 2, wherein the saccharide is a polysaccharide which is biologically active.

18. A method according to claim 2, wherein the substrate is selected from polymeric objects aminated on the surface thereof.

19. A method according to claim 2, wherein the substrate is provided with a coating of polyethylenimine or chitosan.

20. Conjugate made by the method according to claim 2.

21. A method according to claim 3, wherein the borohydride is sodium borohydride or potassium borohydride.

* * * * *